US008129157B2

(12) United States Patent
Gonzalez

(10) Patent No.: US 8,129,157 B2
(45) Date of Patent: Mar. 6, 2012

(54) ANAEROBIC FERMENTATION OF GLYCEROL

(75) Inventor: Ramon Gonzalez, Houston, TX (US)

(73) Assignee: William Marsh Rice University, Houston, TX (US)

( * ) Notice: Subject to any disclaimer, the term of this patent is extended or adjusted under 35 U.S.C. 154(b) by 624 days.

(21) Appl. No.: 12/295,609

(22) PCT Filed: Mar. 30, 2007

(86) PCT No.: PCT/US2007/065726
§ 371 (c)(1),
(2), (4) Date: Sep. 30, 2008

(87) PCT Pub. No.: WO2007/115228
PCT Pub. Date: Oct. 11, 2007

(65) Prior Publication Data
US 2009/0186392 A1   Jul. 23, 2009

Related U.S. Application Data

(60) Provisional application No. 60/788,512, filed on Mar. 31, 2006, provisional application No. 60/867,581, filed on Nov. 28, 2006.

(51) Int. Cl.
*C12P 7/06*         (2006.01)
(52) U.S. Cl. ........ 435/161; 435/141; 435/157; 435/159; 435/160; 435/170
(58) Field of Classification Search .......... None
See application file for complete search history.

(56) References Cited

U.S. PATENT DOCUMENTS
6,303,352 B1   10/2001   Cameron et al.

OTHER PUBLICATIONS

Altaras et al., Biotechnol Prog., 2000, vol. 16, p. 940-946.*
Gokran et al., Applied and Environmental Microbiology, 2000, vol. 66, No. 5, p. 1844-1850.*
Cameron et al., Biotechnol. Prog.1998, vol. 14, p. 116-125.*
Bouvet et al., Res. Microbiol., 1995, vol. 146, p. 279-290.*
Bachler, C., et al., B. *Escherichia coli* dihydroxyacetone kinase controls gene expression by binding to transcription factor DhaR. EMBO J. 24:283-293 (2005).
Berrios-Rivera, et al., The effect of carbon sources and lactate dehydrogenase deletion on 1,2 propanediol production in *Escherichia coli*. J. Ind. Microbiol. Biotechnol. 30:34-40 (2003).
Crabtree, S., et al., Optimize glycol production from biomass. Hydrocarbon Processing: 87-92 (2006).
Datsenko, K.A., et al., One-step inactivation of chromosomal genes in *Escherichia coli* K-12 using PCR products. Proc. Natl. Acad. Sci. U.S.A. 97:6640-5 (2000).
Dharmadi, Y., et al., A better global resolution function and a novel iterative stochastic search method for optimization of HPLC separation. J. Chromatogr. A. 1070:89-101 (2005).
Dharmadi, Y., et al., Anaerobic fermentation of glycerol by *Escherichia coli*: a new platform for metabolic engineering. Biotechnol. Bioeng. 94:821-829 (2006).
Gonzalez, R., et al., A new model for the anaerobic fermentation of glycerol in enteric bacteria: trunk and auxiliary pathways in *Escherichia coli*. Metabolic Engineering 10:234-245 (2008).
Jin, R.Z., et al., Experimental evolution of a novel pathway for glycerol dissimilation in *Escherichia coli*. J. Mol. Evol. 19:429-436 (1983).
Kang Y., et al., Systematic mutagenesis of the *Escherichia coli* genome. J Bacteriol 186:4921-4930 (2004).
Neidhardt, F.C., et al., Culture medium for enterobacteria. J. Bacteriol. 119:736-747 (1974).
Qatibi, et al., Glycerol and propanediols degradation by Desulflvibrio alcoholovorans in pure culture in the presences of sulfate, or in syntrophic asociation with Methanospirillum hungatel. FEMS Microbiology Ecology 85:233-240 (1991).
Schomburg I., et al., BRENDA, the enzyme database: updates and major new developments. Nucleic Acids Res. D431-433 (2004).
Tanaka, S., et al., Replacement of a phosphoenolpyruvate-dependent phosphotransferase by a nicotinamide adenine dinucleotide-linked dehydrogenase for the utilization of mannitol. J. Bacteriol. 93:642-648 (1967).
Tang, J.C., et al., Immunochemical properties of NAD+-linked glycerol dehydrogenases from *Escherichia coli* and *Klebsiella pneumoniae*. J. Bacteriol. 152:1169-1174 (1982).
Tang, J.C., et al., Derepression of an NAD-linked dehydrogenase that serves an *Escherichia coli* mutant for growth on glycerol. J. Bacteriol. 152:1001-1007 (1982).
Tao, H., et al., Engineering a homo-ethanol pathway in *Escherichia coli*: increased glycolytic flux and expression levels of glycolytic genes during xylose fermentation. J. Bacteriol. 183:2979-2988 (2001).
Sprenger et al., Anaerobic Growth of *Escherichia coli* on Glycerol by Importing Genes of the dha Regulon from *Klebsiella pneumoniae*, Journal of General Microbiology (1989), vol. 135, pp. 1255-1262.
Daniel et al., Biochemical and Molecular Characterization of the Oxidative Branch of Glycerol Utilization by *Citrobacter freundii*, Journal of Bacteriology (1995), pp. 4392-4401.

* cited by examiner

*Primary Examiner* — Kade Ariani
(74) *Attorney, Agent, or Firm* — Boulware & Valoir

(57) ABSTRACT

The invention relates to the development of appropriate cultivation conditions for a bacteria to grow anaerobically (fermentatively) on a glycerol substrate. The method requires culturing bacteria having a functional 1,2-propanediol pathway and a functional type II glycerol dehydrogenase-dihydroxyacetone kinase pathway in a culture medium containing high concentrations of glycerol, a neutral to mildly acidic pH, low levels of potassium and phosphate, and high levels of $CO_2$, such that glycerol is thus converted into a desirable product, such as ethanol, hydrogen, formate, succinate, or 1,2-propanediol.

28 Claims, 3 Drawing Sheets

▲ = Cell growth; ■ = glycerol; ● = ethanol; ◆ = succinate; ✻ = formate *plus* acetate Line = Ethanol
Open bar = Formic acid
Shaded bar = $H_2$
I = MG1655, pH 6.3, 10% $CO_2$
II = $\Delta hycB$: pH 7.5, Argon Shaded bar = succinic acid
I = MG1655, pH 6.3, Argon
II = MG1655, pH 6.3, 10%$CO_2$,
III = MG1655, pH 7.5, 20% $CO_2$
IV = $\Delta dhaKLM$(pZSKLcf), pH 7.5, 20% $CO_2$

ANAEROBIC FERMENTATION OF GLYCEROL

CROSS-REFERENCE TO RELATED APPLICATIONS

This application is a 35 U.S.C. Section 371 of PCT/US2007/065726 filed Mar. 30, 2007 which claims priority to U.S. Provisional Applications 60/788,512 filed Mar. 31, 2006, and 60/867,581, filed Nov. 28, 2006, both incorporated herein by reference in their entirety.

FEDERALLY SPONSORED RESEARCH STATEMENT

This invention was made with government support under Grant No: 2005-35504-16698 awarded by United States Department of Agriculture. The government has certain rights in the invention.

REFERENCE TO MICROFICHE APPENDIX

Not applicable.

FIELD OF THE INVENTION

The invention relates to the development of appropriate cultivation conditions for bacteria to grow fermentatively (i.e., in the absence of electron acceptors) on a glycerol substrate. The invention has particular uses for the development of methods and strains able to convert glycerol into higher value products, such as ethanol, hydrogen, formate, succinate, and 1,2-propanediol.

BACKGROUND OF THE INVENTION

Large amounts of glycerol are produced as a by product in the production of biodiesel, and the production of glycerol is predicted to continue to increase because of the tremendous global growth in the production of biodiesel. The current surplus of glycerol has already resulted in a ~10 fold reduction in price in the last two years.

Crude glycerol, therefore, has become an attractive carbon source for fermentation processes, in part because of its low cost. Not only is glycerol abundant, but its higher reduced state, compared to cellulosic sugars, promises to significantly increase the product yield of chemicals whose production from sugars is limited by the availability of reducing equivalents. Taking advantage of the higher reduced state of carbon in glycerol would require the use of anaerobic fermentations (i.e., otherwise the electron acceptor will "take" the electrons instead of being "deposited" in the desired product, including fuels or reduced compounds). The potential use of glycerol as carbon source in fermentation processes could be hampered, however, by the inability of industrial microorganisms, such as *Escherichia coli* (the workhorse of modern biotechnology) to ferment glycerol in the absence of external electron acceptors. The ability to ferment glycerol is restricted to very few organisms, most of them not amenable to industrial applications due to pathogenicity, requirement of strict anaerobic conditions, lack of physiological knowledge and genetic tools for their modification, and high nutritional requirements.

Glycerol can be directly oxidized by the enzyme glycerol dehydrogenase (GldA, encoded by gldA) generating dihydroxyacetone (DHA). However, GldA, which is characterized as a type II glycerol dehydrogenase (glyDH-II), is thought to be cryptic or not expressed in wild type *E. coli* strains. Activation of GldA in *E. coli* required inactivation of glpK, glpR, and glpD followed by a mutagenesis and selection procedure which resulted in a mutant strain that recovered its ability to metabolize glycerol (Jin et al., 1983; Tanh et al., 1982a, b). However, even in this mutant strain, GldA did not provide *E. coli* with the ability to fermentatively metabolize glycerol (Jin et al., 1983; Tanh et al., 1982a, b).

What is needed in the art is a method of bioconverting the global surplus of inexpensive glycerol into other feedstock chemicals. The method would be specially advantageous should it be based on anaerobic fermentation to take advantage of higher reduced state of carbon in glycerol. An anaerobic process would also offer cost advantages, as their counterpart aerobic processes require higher capital investment and exhibit higher operational costs.

SUMMARY OF THE INVENTION

We have discovered that *E. coli* is in fact able to ferment glycerol in the absence of electron acceptors under certain conditions. Our findings represent a new paradigm for glycerol fermentation in *E. coli* and other enteric bacteria and will enable the development of microbial platforms to convert low-value raw glycerol into higher-value chemicals and fuels.

A method of glycerol fermentation is described where pH, $CO_2$ concentration, glycerol concentration, potassium concentration, phosphate concentration, and hydroxyacetone (HA) concentrations are controlled to allow the fermentative metabolism of glycerol to desired chemical precursors.

Improved glycerol fermentation can be obtained when the pH is almost neutral or mildly acidic. In a preferred embodiment, the pH is 5.5-7.5, more preferred is pH 6.0-6.5, in a most preferred embodiment the pH is about 6.3.

$CO_2$ concentrations are inevitably linked to pH and go down as pH increases because $CO_2$ gets converted to bicarbonate, $HCO_3^-$. By increasing $CO_2$ to 20-30% the negative effects of increased pH above 7.0 can be reduced. Improved glycerol fermentation was seen with pH 6.3 and 10% $CO_2$, pH 7.5 and 20% $CO_2$. Greater concentrations of $CO_2$ were also beneficial.

Given the high-reduced state of carbon in glycerol, maintaining redox balance becomes very "delicate" because incorporation of glycerol into cell mass results in the net generation of reducing equivalents. H2 serves as electron donor in several reactions (e.g., fumarate reductase) and thus offsets the redox balance. If H2 concentration is decreased, this does not happen and glycerol fermentation proceeds optimally. By increasing headspace, H2 was diluted and glycerol fermentation was improved. Flushing the headspace with inert gas or CO2 removes excess H2 and further increases glycerol fermentation. Sparging, or bubbling gas through the culture, removed the most H2 and provided the best glycerol fermentation conditions.

Improved glycerol fermentation can be obtained when glycerol feedstock concentrations are high, for example greater than 5 or 10 g/L, or even greater (25 g/L, 50 g/L, 75 g/L, 100 g/L). In a preferred embodiment glycerol concentrations are greater than 100 g/L.

Improved glycerol fermentation can be obtained with low potassium and low phosphate concentrations. Potassium concentrations were preferably less than 10 mM, more preferably less than 5 or 2 mM, and most preferably less than 0.6 mM. Phosphate concentrations were preferably less than 50 mM, more preferably less than 25 or 10 mM. More preferred is less than 5 mM and most preferably less than 1.3 mM. Low phosphate and potassium favor the operation of the glycerol dehydrogenase-dihydroxyacetone kinase and 1,2-PDO pathways, the latter enabling redox-balanced conditions.

Supplementing the culture with HA (at least 10, 20, or 30 mM), further improved culture conditions. Tryptone supplementation was not required when the culture was supplemented with HA.

In one embodiment, glycerol fermentation was optimized by culturing *E. coli* with 10 g/L glycerol at pH 6.3 with 0.6 mM potassium, and 1.3 mM phosphate at 37° C. while sparging with $CO_2$, Ar, or $N_2$.

In, other embodiments, the invention can be used for specific applications such as the synthesis of desired end products, such as succinate, ethanol, formate or hydrogen, and 1,2-PDO using glycerol as a carbon source.

DESCRIPTION OF EMBODIMENTS OF THE INVENTION

Figure 1:
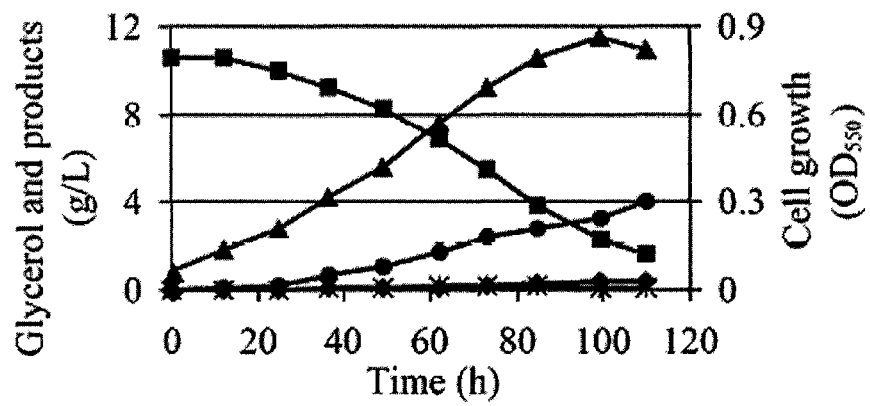
FIG. 1. Fermentation of glycerol by *E. coli* MG1655 in minimal medium (MM) supplemented with 2 g/L tryptone. Cell growth (▲), glycerol consumption (■), and accumulation of ethanol (●), succinate (♦), and formate plus acetate (✱).

The invention provides a novel method of fermenting glycerol with bacteria to produce useful chemical compounds.

A "cryptic" gene is one that is not expressed or conditions for gene expression are unknown.

"Disproportionate" is to oxidize and reduce.

The terms "disruption" and "disruption strains," as used herein, refer to cell strains in which the native gene or promoter is mutated, deleted, interrupted, or down-regulated in such a way as to decrease the activity of the enzyme encoded thereby. A gene is completely (100%) reduced by knockout or removal of the entire genomic DNA sequence. Use of a frame shift mutation, early stop codon, point mutations of critical residues, or deletions or insertions, and the like, can completely inactivate (100%) gene product by completely preventing transcription and/or translation of active protein.

"Dissimilation" is the metabolic process by which organisms convert substances into excreted compounds.

The term "exogenous" indicates that the protein or nucleic acid is a non-native molecule introduced from outside the organism or system without regard to species of origin. For example, an exogenous peptide may be applied to the cell culture; an exogenous RNA may be expressed from a recombinant DNA transfected into a cell; or a native gene may be under the control of exogenous regulatory sequences.

By "fermentation" what is meant is metabolism or dissimilation of a carbon source in the complete absence of external electron acceptors: no oxygen, no nitrate, etc.

By "functional 1,2-propanediol pathway" what is meant is that the bacteria functionally express the genes (and thus enzymes) needed to make 1,2-PDO by one or more different routes. For example, functional mgsA (methylglyoxal synthase: MGS), yeaE, yghZ, and yafB genes (aldo-keto reductase: AKR), gldA (glycerol dehydrogenase, GldA) are each required. An important distinction is that a given organism might have the genes/enzymes of an specific pathway but the pathway is cryptic.

By "functional type II glycerol dehydrogenase-dihydroxyacetone kinase pathway" what is meant is that the bacteria have the enzymes needed to make DHA phosphate (DHAP) from glycerol in the absence of external electron acceptors by converting glycerol to DHA to DHAP. For example, the bacteria must have active GldA (gldA) and DHA kinase (DHAK: dhaKLM).

By "functional $F_0F_1$ ATP synthase pathway" what is meant is that the bacteria have all of the enzymes needed to couple ATP synthesis with the proton pump. For example, the bacteria must have functioning atp operons, including atpF and atpD.

By "functional formate-hydrogen lyase (FHL) pathway" what is meant is that the bacteria have all of the enzymes needed to disproportionate formate to $CO_2$ and hydrogen. For example, active formate dehydrogenase (e.g., FDH-F: fdhF) and hydrogenase 3 (hyc operons).

By "functional 1,3-propanediol pathway" what is meant is the genes or enzymes required to make 1,3-PDO. For example, glycerol dehydratase (GD) and/or 1,3-PDO reductase (1,3-PDOR) are inactive or absent in a cell that lacks a functional 1,3-propanediol pathway.

"Glycerol" is described at NCBI™ PubChem #753 and CAS Reg #56-81-5, incorporated herein by reference.

By "overexpressed" what is meant is that the gene (or protein) are modified so as to have increased activity as compared with wild type. This can be done by adding more copies of a gene to a cell, by mutating the gene to delete inhibitory sequences, by removing inhibitors, or by changing the protein to increase activity, and the like.

As used herein "recombinant" is relating to, derived from, or containing genetically engineered material.

"Reduced activity" or "inactivate" is defined herein to be at least a 75% reduction in protein activity, as compared with an appropriate control species. Preferably, at least 80, 85, 90, or 95% reduction in activity is attained, and in the most preferred embodiment, the activity is eliminated (100%). Proteins can be inactivated with inhibitors, by mutation, or by suppression of expression or translation, and the like. By "null mutant" or "null mutation" what is meant is that protein activity is completely inactivated. In one example, the control plasmid is inserted without the gene of interest. In another example, the gene of interest is completely removed by recombination. Additionally, the gene of interest may be removed by inactivation, mutation, or truncation which eliminates activity.

The terms "succinate" and "succinic acid" and "formate" and "formic acid" are used interchangeably herein. Chemicals herein can be found in the NATIONAL LIBRARY OF MEDICINE® PUB CHEM™ database (pubchem.ncbi.nlm.nih.gov) incorporated herein by reference. Bacterial metabolic pathways can be found in *Principles of Biochemistry* 2$^{nd}$ ed., by Lehninger (1993), incorporated herein by reference, as well as many other biochemistry texts.

TABLE 1

Genes and Enzymes

| Gene | (Abbreviation) Protein name (Acc. No.) |
|---|---|
| adhE | acetaldehyde-CoA dehydrogenase (GenBank # NP_415757) |
| atpD | $F_0F_1$ ATP synthase subunit beta (GenBank # NP_418188) |
| atpF | $F_0F_1$ ATP synthase subunit B (GenBank # NP_418192) |
| cydA | cytochrome D terminal oxidase, subunit I (GenBank # NP_415261) |
| cyoB | cytochrome O ubiquinol oxidase, subunit I (GenBank # NP_414965) |
| dhaK | (DHAK) dihydroxyacetone kinase subunit K (N-terminal domain at GenBank # NP_415718) |
| dhaK | (DHAK) dihydroxyacetone kinase, subunit 1 from *Citrobacter freundii* (GenBank # AAB48843) |
| dhaL | (DHAL) dihydroxyacetone kinase subunit L (C-terminal domain at GenBank # NP_415717) |
| dhaM | (DHAM) dihydroxyacetone kinase subunit M (fused phosphotransferase subunit at NP_415716) |
| fdhF | formate dehydrogenase-H, FDH (selenopolypeptide subunit at GenBank # NP_418503) |
| fixA | (ETF) electron transfer flavoprotein (GenBank # NP_414583) |
| frdA | (Frd) fumarate reductase (GenBank # NP_418578) |
| fucO | (FucO) L-1,2-propanediol oxidoreductase (GenBank # NP_417279) |
| gldA | (GDHA) glycerol dehydrogenase (GenBank # NP_418380) |
| glpA | anaerobic sn-glycerol-3-phosphate dehydrogenase (GenBank # NP_416744) |
| glpD | aerobic sn-glycerol-3-phosphate dehydrogenase (GenBank # NP_417884) |
| hycB | hydrogenase 3 part of formate hydrogen lyase (FHL) complex (Fe—S subunit at GenBank # NP_417204) |
| mgsA | methylglyoxal synthase (GenBank # NP_415483) |
| pta | phosphate acetyltransferase (GenBank # NP_416800) |
| trkA | potassium ion transporter peripheral membrane component (GenBank # NP_417748) |
| yafB | 2,5-diketo-D-gluconate reductase B (GenBank # NP_414743) |
| yeaE | Aldo/keto reductase (GenBank # NP_754080) |
| yghZ | Aldo/keto reductase (GenBank # NP_417474) |
| dhaR | (dhaS or dhaR) HTH-type dhaKLM operon transcriptional activator |

EXAMPLE 1

Materials and Methods

Throughout the application, gene disruption mutants are referred to using the following nomenclature: Δgene1 for a single disruption of gene1 or Δgene1Δgene2 for a double disruption.

Wild-type *E. coli* K12 strains MC4100 (ATCC 35695), W3110 (ATCC 27325), wild-type *E. coli* B (ATCC 11303), and enteric bacteria *Enterobacter cloacae* subsp. *cloacae* NCDC 279-56 (ATCC 13047), *Buttiauxella agrestis* (ATCC 33994), *Serratia plymuthica* (ATCC 15928), and *Leminorella richardii* (ATCC 33998) were obtained from the AMERICAN TYPE CULTURE COLLECTIONS. Single mutant recombinant strains Δpta, ΔadhE, ΔcydA, ΔcyoB, ΔfrdA, ΔfixA, ΔglpA, ΔglpD, ΔmgsA, ΔyeaE, ΔyghZ, ΔyafB, ΔfucO, ΔatpF, ΔatpD, ΔpykF, and ΔhycB were obtained from the *E. coli* Genome Project (University of Wisconsin-Madison, www.genome.wisc.edu) or constructed using the method described by Datsenko and Wanner (2000). K12 strain MG1655 (F— lambda-ilvG-rfb-50 rph-1) was used as wild-type for creating gene disruption mutants. Strains ΔgldA, ΔdhaKLM, and ΔfdhF were constructed in both MG1655 and W3110 (ATCC 27325). Multi-gene disruptions were achieved by combining single mutations through the use of P1 phage transduction. Each mutation was added to the strain one at a time after removing the kanamycin cassette.

Plasmids pZSKLM (expressing *E. coli* DHA kinase subunits DhaKLM), and pZSKLcf (expressing *Citrobacter freundii* DHA kinase subunits DhaKL) were kindly provided by Dr. B. Erni, Universitat Bern, Switzerland (Bachler et al., 2005). Plasmid pZSKLM_gldA, expressing enzymes DHAK and GldA was constructed as follows. The complete open reading frame of gldA gene along with its ribosomal binding site was PCR amplified. The PstI and MluI sites were introduced through the primer to both the ends of PCR product to facilitate cloning of gldA gene downstream of dhaKLM operon in the plasmid pSZKLM. Both plasmid and PCR product were digested with PstI and MluI, ligated, transformed in DH5α and screened for positive colonies. Successful construction of the plasmid was verified via PCR and through the characterization of encoded enzyme activities. Plasmids were transformed into *E. coli* strains and selected on Luria Bertani (LB) supplemented with appropriate antibiotics.

Standard recombinant DNA procedures were used for cloning, plasmid isolation, phage P1 transduction, electroporation, and polymerase chain reaction (PCR) (Sambrook et al., 1989). The strains were kept in 32.5% glycerol stocks at −80° C. Plates were prepared using LB medium containing 1.5% agar. Antibiotics and inducers were included as appropriate at the following concentrations: 100 μg/ml ampicillin, 30 μg/ml chloramphenicol, 50 μg/ml kanamycin, and 12.5 μg/ml tetracycline, 0.001-0.1 mM IPTG, and 100 ng/ml anhydrotetracycline.

The minimal medium (MM) designed by Neidhardt et al. (1974) supplemented with 0.03-0.2% tryptone, 5 μM selenyle, and 1.32 mM $Na_2HPO_4$ in place of $K_2HPO_4$ was used, unless otherwise specified. MOPS (3-(N-Morpholino)propanesulfonic acid) itself was only included in experiments conducted in tubes (see below) or in experiments where no tryptone supplementation was used. When indicated, the medium was supplemented with specified concentrations of the following compounds: monobasic and dibasic sodium and potassium phosphates, monobasic and dibasic ammonium phosphates, sodium chloride, sodium sulfate, potassium chloride, potassium sulfate, L-amino acids, nucleotides, and vitamins. All chemicals were obtained from SIGMA-ALDRICH® Co. (St Louis, Miss.) unless otherwise specified.

All experiments were conducted under anaerobic conditions and, unless otherwise noted, at 37° C. Experiments in tubes were conducted in sealed anaerobic tubes (HUNGATE™ tubes: BELLCO GLASS® Inc., NJ, USA) either completely filled with media or continuously sparged with argon (initial pH 7.2). The fermentation systems and its operation under anaerobic conditions along with inoculum preparation techniques have been described elsewhere (Dharmadi et al., 2006).

Prior to use, the stock cultures (stored as glycerol stocks at −80° C.) were streaked onto LB plates and incubated overnight at 37° C. in an OXOID™ anaerobic jar with the $CO_2$ gas generating kit (OXOID® Ltd, Basingstoke, Hampshire, UK). A single colony was used to inoculate 17.5 mL HUNGATE™ tubes completely filled with medium (MM supplemented with 10 g/L tryptone, 5 g/L yeast extract, and 5 g/L glycerol). The tubes were incubated at 37° C. until an $OD_{550}$ of ~0.4 was reached. An appropriate volume of this actively growing pre-culture was centrifuged and the pellet washed and used to inoculate 350 mL of medium in each fermentor, with the target starting optical density of 0.05 at 550 nm.

Fermentations were conducted in a SIXFORS™ multi-fermentation system (INFORS® HT, Bottmingen, Switzerland) with six 500 ml working volume vessels and independent control of temperature, pH, and stirrer speed (200 rpm.). The system was fully equipped and computer controlled using manufacturer IRIS NT software. Each vessel was fitted with a condenser to prevent evaporation, which was operated with a 0° C. cooling methanol-water supply. Anaerobic conditions were maintained by flushing the headspace with ultra-high purity argon (MATHESON TRI-GAS®, Inc., Houston, Tex.) at 0.01 LPM. An oxygen trap (ALLTECH ASSOCIATES®, Inc., Deerfield, Ill.) was used to eliminate traces of oxygen from the gas stream. To maintain sterility, 0.2-μm and the 0.45-μm HEPA filters (MILLIPORE®, Billerica, Calif.) were used to fit the inlet and outlet lines, respectively.

Optical density was measured at 550 nm and used as an estimate of cell concentration (1 O.D.=0.34 g DW/L). After centrifugation, the supernatant was stored at −20° C. for HPLC analysis. To quantify the concentrations of glycerol, lactate, acetate, formate, succinate, and ethanol, samples were analyzed with ion-exclusion HPLC using a SHIMADZU PROMINENCE SIL 20™ system (SHIMADZU SCIENTIFIC INSTRUMENTS® Inc., Columbia, Md.) equipped with an HPX-87H organic acid column (BIO-RAD®, Hercules, Calif.). Operating conditions to optimize peak separation (30 mM $H_2SO_4$ in mobile phase, column temperature 42° C.) were determined using a previously described approach (Dharmadi and Gonzalez, 2005). Hydrogen production was measured in selected samples using gas chromatography. Hydrogen could also be calculated as the difference between molar amounts of (ethanol+acetate) and formate. 1,2-PDO concentrations were determined via NMR (nuclear magnetic resonance) experiments as described below and using tetramethylsilane (TMS) as standard.

The identities of the fermentation products were confirmed through a 1D 1H (Proton) NMR experiment. 60 μl $D_2O$ and 1 μl of 600 mM NMR internal standard TSP (3-(Trimethylsilyl) propionic acid-D4, sodium salt) were added to 540 μl of the sample. The resulting solution was then transferred to a 5 mm-NMR tube and 1D proton NMR spectroscopy was performed at 25° C. in a VARIAN® 500 MHz INOVA™ spectrometer equipped with a PENTA™ probe. The following parameters were used: 8,000 Hz sweep width; 2.8 second acquisition time; 256 acquisitions; 6.3 As pulse width; 1.2 s pulse repetition delay; and presaturation for 2 seconds. The resulting spectrum was analyzed using the software FELIX™ 2001 (ACCELRYS SOFTWARE® Inc., Burlington, Mass.). Peaks were identified by their chemical shifts and the J-coupling values, which were obtained in separate experiments where samples were spiked with metabolite standards (2 mM final concentration).

Further characterization of the samples was achieved through a 2D 1H-1H COSY (COrrelation SpectroscopY) NMR experiment. A double-quantum filtered COSY spectrum with Watergate solvent suppression was obtained using the wgdqfcosy pulse sequence that is part of the BIO PACK™ suite of pulse sequences (VARIAN®, Inc.). The following parameters were used: 6,000 Hz sweep width; 0.5 second acquisition time; 600 complex points in t1 dimension; 32 transients; 5.5 μs pulse width; and 1 second relaxation delay.

Incorporation of glycerol into proteinogenic biomass was assessed by fermenting 50% U-13C-labeled glycerol in *E. coli*. After 3 days (72 hrs), tubes were harvested and the fermentation broth was centrifuged. The cell pellets were washed once with 9 g/L NaCl solution and centrifuged again. The resulting cell pellets were hydrolyzed with 6N constant boiling HCl at 110° C. for 24 hours using the REACTI-THERM™ hydrolysis system (PIERCE®, Rockford, Ill.). To remove HCl, the resulting solution was subjected to rapid vaporization at 75° C. under vacuum for 2 hours using the CENTRIVAP™ system (LABCONCO® Corp., Kansas City, Mo.). The dried sample was reconstituted in 1 ml $D_2O$ (Cambridge Isotope Laboratories, Cambridge, Mass.), frozen to −80° C., and subsequently freeze-dried in the 4.5 L FREE ZONE™ freeze dry system (LABCONCO® Corp) for 24 hours. The sample was then reconstituted in 600 μl $D_2O$ and filtered to remove cell particulates. One μl TSP standard was added to the sample, and the contents were transferred to an NMR tube. To determine $^{13}C$ enrichment, the samples were analyzed using 1D proton spin echo with and without concurrent 90° pulses on carbon[50]. The 90° pulse on carbon refocused the $^{13}C$ carbon atoms, thereby suppressing the $^{13}C$ satellites arising due to proton-carbon spin coupling. This phenomenon did not occur for the $^{12}C$ carbon atoms. For these experiments, we used the commercially available pulse sequence pwxcal on 500 MHz Varian INNOVA™ spectrometer. The following parameters were used: 8,000 Hz sweep width; 2.7 second acquisition time; 256 transients; and pwx10 and 90° at 25° C. Individual amino acids were identified based on chemical shifts and the fine structure of the spectra.

To perform enzymatic assays, cells from anaerobic cultures of an $OD_{550}$ of ~0.7 were harvested by centrifugation (2 min, 10,000×g), washed with 9 g/liter NaCl, and stored as cell pellets at −20° C. Cells were resuspended in 0.2 ml of the respective buffer and permeabilized by vortex mixing with chloroform (Tao et al., 2001). Glycerol dehydrogenase was assayed by measuring the change in absorbance at 340 nm and 25° C. in a mixture containing 50 mM Tris.HCl (pH 7.6), 2 mM $MgCl_2$, 500 μM NAD+, 10 mM glycerol, and 10-100 μl crude cell extract. Glycerol dehydrogenase activity with HA, methylglyoxal reductase activity, aldo-keto reductase activity, and linearity of the reactions (protein concentration and time) were established for all preparations. Results were expressed as micromoles minute$^{-1}$ milligram of cell protein$^{-1}$ and were averages for at least three cell preparations.

Specific rates for cell growth (μ), glycerol consumption, and product synthesis were estimated by plotting total cell, glycerol, or product concentration versus the integral of cell concentration (ICC), and fitting these plots to polynomial functions.

EXAMPLE 2

Glycerol Fermentation and Effect of Medium Composition

Although it is believed that glycerol metabolism in *E. coli* is restricted to respiratory conditions, we have discovered that this organism can metabolize glycerol in the absence of electron acceptors. FIG. 1 shows a typical fermentation profile for wild-type strain MG1655 in a medium supplemented with 2 g/L tryptone (additional details were provided in provisional applications 60/788,512 and 60/867,581 and Gonzalez et al., 2007). Approximately 1-2 g/L of glycerol were left unfermented in the medium of stationary phase cultures. Ethanol, 1,2-propanediol (1,2-PDO), and succinic, acetic, and formic acids were identified as fermentation products using different NMR techniques.

We next sought to identify the effect of various parameters on glycerol fermentation. Potassium, phosphate, sodium, glycerol, HA, pH and $CO_2$ were titrated for cell growth according to typical methods.

Figure 2:
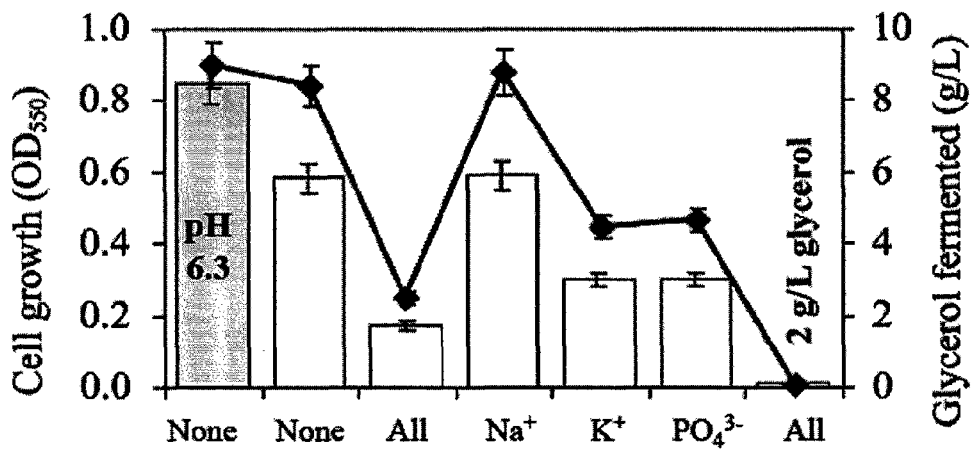
FIG. 2. Effect of concentration of $Na^+$, $K^+$, $PO_4^{3-}$, and glycerol. $Na^+$ (34 mM), $K^+$ (128 mM), and $PO_4^{3-}$ (98 mM) were added to the medium as indicated. Unless otherwise noted, experiments were conducted at pH 7.5, 37° C., 10 g/L glycerol, 2 g/L tryptone, and flushing the headspace with argon. Glycerol fermentation (line) and cell growth (bars) are shown: bar color indicates pH 6.3 (gray) or 7.5 (white).

The typical media used in previous studies of glycerol metabolism in E. coli contained high levels of phosphate, potassium, and sodium whose main purpose was to control the pH of the culture from 7-7.5. This medium was initially reported by Tanaka et al. (1967) and subsequently used by most investigators in studies of glycerol metabolism in E. coli. We have found that supplementing our medium with such levels of phosphate, potassium, and sodium (i.e., 34 mM $NaH_2PO_4$ and 64 mM $K_2HPO_4$) severely impaired glycerol fermentation (FIG. 2)—an effect that is particularly detrimental at alkaline pH. Potassium and phosphate, but not sodium, were responsible for the negative effect (FIG. 2). The analysis of glycerol consumption patterns in our experiments showed that significant amounts of glycerol remained unmetabolized in the medium (typically 10-30 mM), suggesting the existence of a threshold concentration that limits the anaerobic fermentation of glycerol. Interestingly, previous studies of glycerol metabolism were also conducted at concentration of glycerol typically ranging from 20 to 30 mM. We now know that glycerol fermentation and cell growth were completely impaired when using a medium containing high levels of phosphate and potassium, 2 g/L of glycerol, and conducting the fermentation at pH 7.5 and 37° C. (FIG. 2).

Taken together, our results clearly demonstrate that previous attempts to anaerobically ferment glycerol using E. coli were not successful because the experiments were all conducted at conditions that negatively affect glycerol fermentation. Such conditions include the use of neutral to alkaline pH (7-7.5), high concentrations of potassium and phosphate, relatively low concentrations of glycerol, 37° C., and closed vessels. The latter is a condition we have shown to impair glycerol fermentation due to the accumulation of hydrogen and the resulting effect on redox balance.

EXAMPLE 3

Pathways and Mechanisms of Glycerol Fermentation

The anaerobic fermentation of glycerol in enteric bacteria has long been considered a privilege of species that have an active 1,3-PDO pathway. We have demonstrated, however, that E. coli can fermentatively metabolize glycerol in a 1,3-PDO-independent manner, so long as a functioning 1,2-PDO pathway and glyDH-II-DHAK pathways were present.

Figure 3:
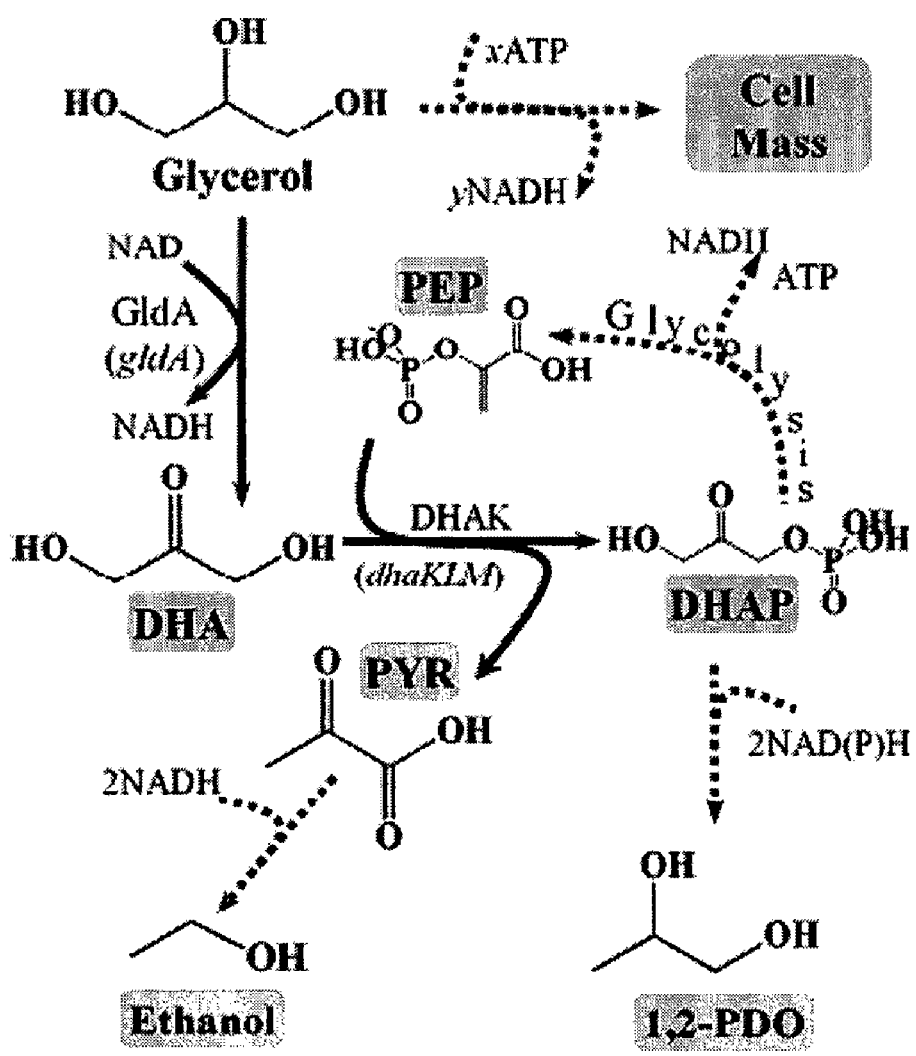
FIG. 3. A new paradigm for glycerol fermentation in *E. coli* and other enteric bacteria possessing a type II glyDH. The proposed pathway for the conversion of glycerol to glycolytic intermediate DHAP in *E. coli* is composed of enzymes GldA and DHAK.

Based on our findings, described in more detail in Dharmadi, et al. (2006), Gonzalez et al., 2007, and provisional applications 60/867,581 and 60/788,512 (each incorporated by reference), we propose a new paradigm for glycerol fermentation in enteric bacteria in which: (i) the 1,2-PDO pathway provides a means to consume reducing equivalents generated during synthesis of cell mass, thus enabling redox balanced conditions and (ii) the synthesis of ethanol, through a redox-balanced pathway, fulfills energy requirements by generating ATP via substrate-level phosphorylation (FIG. 3). The activity of the formate hydrogen-lyase and $F_0F_1$-ATPase systems were also found to facilitate the fermentative metabolism of glycerol probably by helping to maintain intracellular pH and $CO_2$ supply. We showed that the pathway converting glycerol into glycolytic intermediates is composed of two enzymes (FIG. 3): a glycerol dehydrogenase (glyDH) and a DHA kinase (DHAK), the former of previously unknown physiological role.

TABLE 2

Cell growth during fermentation of glycerol[1,2]

| Strain | GldA Protein | Growth Rate $\mu_M \pm SD^3$ | Growth Yield $Y_{X/S} \pm SD^4$ | 1,2-PDO[5] (mM) |
|---|---|---|---|---|
| W3110 | glyDH-II | 0.031 ± 0.002 | 32.2 ± 3.1 | YES |
| MG1655 | glyDH-II | 0.040 ± 0.003 | 32.9 ± 2.9 | YES |
| MC4100 | glyDH-II | 0.029 ± 0.004 | 54.9 ± 8.8 | YES |
| E. coli B | glyDH-II | 0.036 ± 0.002 | 34.1 ± 2.7 | YES |
| E. cloacae | glyDH-II | 0.022 ± 0.002 | 30.9 ± 2.8 | YES |
| L. richardii | glyDH-III | ND | ND | ND |
| B. agrestis | glyDH-IV | ND | ND | ND |
| S. plymuthica | NONE | ND | ND | ND |

[1]Experiments were conducted in the presence of 0.2% tryptone and 10 g/L of glycerol.
[2]NG: no growth observed; ND: none detected; SD: standard deviation.
[3]$\mu_M$: maximum specific growth rate (h$^{-1}$) calculated during exponential growth.
[4]$Y_{X/S}$: growth yield (mg cell/g glycerol) calculated as the increase in cell mass per glycerol consumed.
[5]Synthesis of 1,2-PDO was identified through NMR as described.

Our finding that strain MG1655 can ferment glycerol is a general characteristic of E. coli species, as other tested strains (W3110, MC4100, and E. coli B) were also able to ferment glycerol (Table 2). Since two other glyDHs, namely glyDH-III and glyDH-IV, have been identified in members of Enterobacteriaceae, we investigated their involvement in the anaerobic fermentation of glycerol. Only strain Enterobacter cloacae NCDC 279-56, which like E. coli possesses a glyDH-II (2), was able to ferment glycerol (Table 2). Our preliminary results with the yeast Saccharomyces cerevisiae appear to indicate that similar pathways could support glycerol fermentation in this organism.

The above pathways provide a framework to explain the observed effect of pH and concentrations of potassium, phosphate, and glycerol on glycerol fermentation (see EXAMPLE 2, provisional application 60/867,581, and Gonzalez et al., 2007). For example, high levels of phosphate promote the decomposition of both DHA and HA (two key intermediates in the aforementioned pathways) and negatively affect GldA activity and its inducibility by HA. In addition, MG synthase, a key enzyme responsible for 1,2-PDO synthesis, is inhibited by high phosphate levels. High concentrations of potassium increase the toxicity of MG, a key intermediate in the synthesis of 1,2-PDO. The low-affinity of GldA for glycerol [Km is 3-40 mM] explains both the requirement of high concentrations of glycerol for its fermentative metabolism and our observation that 10-30 mM glycerol remained unmetabolized in the medium.

The effect of pH on glycerol fermentation can also be related to its impact on the aforementioned pathways (see EXAMPLE 2, provisional application 60/867,581, and Gonzalez et al., 2007). GldA exhibits strong pH dependence with higher oxidative activity at very alkaline pHs and reductive activity at neutral to alkaline conditions. Acidic conditions reduce not only the activity of glyDH, but also MG-reducing activities, which are required for the synthesis of 1,2-PDO. Alkaline conditions, on the other hand, increase the toxicity of MG, a key intermediate in the synthesis of 1,2-PDO. Clearly, the intracellular pH needs to be carefully controlled to avoid low activities of key enzymes and MG toxicity. For example, while an extracellular pH of 6.3 apparently prevents MG toxicity, the cells would still require a system to prevent the pH from falling below the levels permissible for glyDH and MGR/AKR activities. By converting formic acid to $CO_2$ and $H_2$, the FHL system is known to prevent cytoplasmic acidification, which could explain why FHL is required for glycerol fermentation at acidic conditions. Yet, FHL activity could generate excess hydrogen that, if accumulated, would negatively affect glycerol fermentation. At alkaline conditions, the $F_0F_1$-ATPase system might be required for preventing alkalinization of the cytoplasm, thus avoiding MG toxicity.

EXAMPLE 4

Improvement of Productivity and Feasibility of Glycerol Fermentation in Industrial Media To demonstrate the implications of our findings for the improvement of glycerol fermentation, we overexpressed the discovered trunk pathway (GldA-DHAK) in wild-type strain MG1655 and observed more than 2-fold increase in both cell growth and glycerol fermentation. Amplification of the GldA-DHAK pathway was achieved by transforming MG1655 with plasmid pZSdhaKLM_gldA. Further increases in productivity might require concerted overexpression of glycolytic enzymes (e.g., triose-phosphate isomerase) along with the GldA-DHAK pathway. In addition, several process-based improvements including further optimization of the culture medium, cultivation system, and mode of operation are being implemented.

The application of glycerol fermentation at industrial levels would require the use of glycerol derived during the production of biodiesel. We observed similar cell growth and glycerol fermentation when MG1655 was cultivated on pure glycerol and two samples of glycerol obtained from a biodiesel plant operated by FutureFuel Chemical Company: after 48 hours of cultivation, the cells fermented 4 (pure), 3.9 (refined), and 3.8 (crude) g/L of glycerol and reached an optical density of 1.2 (pure), 0.96 (refined), and 0.98 (crude).

The replacement of tryptone supplementation with cost-effective industrial supplements is another key factor for commercial success. However, we have already demonstrated that medium supplementation with corn steep liquor (an inexpensive supplement used in industrial fermentation) support glycerol fermentation at levels similar to those observed with tryptone supplementation (Dharmadi et al., 2006)

We have also obtained MG1655 mutants capable of growing in minimal medium with no supplementation (an $OD_{550}$ of 0.36 and 8.1 g/L of glycerol fermented). These mutants were generated through multiple rounds of selection for strains able to ferment glycerol in media containing decreasing amounts of HA or tryptone (provisional application 60/867,581).

EXAMPLE 5

Products from Glycerol

Figure 4:
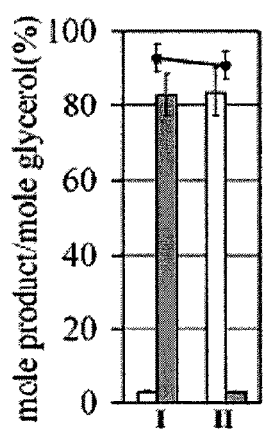
FIG. 4. Co-production of ethanol (line)-$H_2$ (solid bars), and ethanol (line)-formic acid (open bars) during fermentation of glycerol. (I) MG1655: pH 6.3, Argon; (I)) ΔhycB: pH 7.5, Argon. HycB is a required component of the FHL system.
Figure 5:
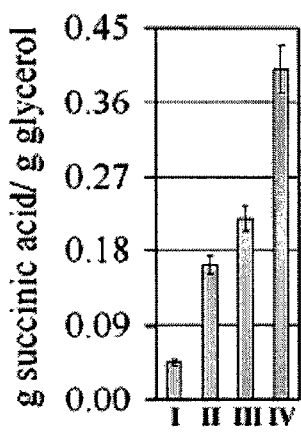
FIG. 5. Production of succinic acid from glycerol: (I) MG1655: pH 6.3, Argon; (II) MG1655: pH 6.3, 10% $CO_2$; (III) MG1655: pH 7.5, 20% $CO_2$; and (IV) ΔdhaKLM (pZSKLcf): pH 7.5, 20% $CO_2$. Plasmid pZSKLcf expresses *C. freundii* DHA kinase subunits DhaKL.

We also made exemplary demonstrations of product formation using glycerol as a carbon source and the media described above. For example, we showed the production of ethanol in FIG. 4. Our results indicated that minor genetic and environmental modifications make *E. coli* a good biocatalyst for the conversion of glycerol to either ethanol and $H_2$—$CO_2$ (pH 6.3) or ethanol and formate (pH 7.5 and disruption of the FHL system). Ethanol production via sugar fermentation, in contrast, would offer the possibility of neither $H_2$ nor formate co-production, thus representing a less efficient process. Further improvements of ethanol-$H_2$ and ethanol-formate yields will result from the elimination of succinate and acetate pathways (frdA and pta mutations: Gonzalez et al., 2007 and provisional application 60/867,581). Improvement in productivities and use of industrial medium is as described above in EXAMPLE 4.

Another example is succinic acid, whose production from sugars is limited by the availability of reducing equivalents. Fortunately, its synthesis from glycerol is feasible through a redox-balanced pathway. However, very low production of succinate from glycerol was observed in our experiments with MG1655, a consequence of glycerol being dissimilated through the PEP-dependent GldA-DHAK pathway (i.e., low PEP availability). By replacing *E. coli* PEP-dependent DHAK with *C. freundii* ATP-dependent DHAK, along with the use of appropriate pH and concentration of $CO_2$, we achieved an almost 10-fold increase in succinate yield (FIG. 4), using the media described above. Further improvements in succinate yield will result from the elimination of ethanol and acetate pathways (adhE and pta mutations: Gonzalez et al., 2007 and provisional application 60/867,581). Improvement in productivities and use of industrial medium is as described above in EXAMPLE 4, with the exception that *C. freundii* ATP-dependent DHAK will be overexpressed instead of native DHAK. To make the succinic acid pathway more energetically favorable we are eliminating *E. coli* phosphoenolpyruvate carboxylase (PEPC, encoded by the gene ppc) and overexpression of phosphoenolpyruvate carboxykinase (PEPCK) from *E. coli* (pckA), *Actinobacillus succinogenes* (pckA) or other microorganisms as described in enzyme database BRENDA (Schomburg et al., 2004). Higher energy production through the succinate pathway (unlike PEPC, PEPCK generates ATP) should result in both higher productivities and yield.

Another product whose synthesis would benefit from the highly reduced state of carbon in glycerol is 1,2-PDO. The amplification of the GldA-DHAK pathway not only resulted in an increased productivity but also led to almost 20-fold increase in the synthesis of 1,2-PDO: while MG1655 produced only 0.026 mM of 1,2-PDO, recombinant strain MG1655 (pZSdhaKLM_gldA) accumulated 0.51 mM of this product. These results are probably due to the involvement of GldA in the synthesis of 1,2-PDO (Gonzalez et al., 2007).

We are now pursuing several strategies to produce high levels of 1,2-PDO from glycerol, which are described as follows:

(1) Replacing the native PEP-dependent DHAK (dhaKLM) of *E. coli* with the ATP-dependent DHAK (dhaKL subunits) of *C. freundii* and its overexpression along with native glycerol dehydrogenase (gldA).

(2) Overexpression of enzymes methylglyoxal synthase, glycerol dehydrogenase, and methylglyoxal reductases, all involved in the conversion of DHAP to 1,2-PDO (Gonzalez et al., 2007 and provisional application 60/867,581).

(3) Increasing the availability of NADPH to drive the conversion of DHAP into 1,2-PDO by improving the conversion of NADH into NADPH through overexpression of transhydrogenases or engineering cofactor specificity of enzymes in the central metabolic routes including glycerol dehydrogenase, glycerol-3-P dehydrogenase, glyceraldehydes dehydrogenase, pyruvate dehydrogenase, etc. Alternatively, variation of these enzymes that in their native form use NADP as cofactor can be cloned from other organisms and expressed in *E. coli*.

(4) Engineering a glycerol dehydratase (GD, which in nature dehydrates glycerol by converting it into 3-hydroxypropionaldehyde) for the conversion of glycerol into HA in one step. HA is then converted to 1,2-PDO by GldA or others enzymes in *E. coli*, as we have already demonstrated in experiments in which HA initially present in the culture medium was stoichiometrically converted to 1,2-PDO (provisional application 60/867,581). This route will avoid methylglyoxal as intermediate (a very toxic product) and represents a more energy efficient route of converting glycerol to 1,2-PDO as no ATP is consumed, resulting in a significant increase in yields. The engineered GD is being obtained by mutagenizing *C. butyricum* GD (dhaB1), which unlike other GDs does not require coenzyme $B_{12}$ for activity. We are also conducting a search for a native microbial GD that could convert glycerol into HA. Once found, this activity will be cloned and expressed in *E. coli.*

(5) Combined chemical (glycerol to HA) and biological (HA to 1,2-PDO) strategy. Dehydration of glycerol to HA has been efficiently achieved with a process that uses a solid catalyst, moderate temperature (~200° C.), and atmospheric pressure (Crabtree et al., 2006). The only products are HA and water. We have demonstrated the efficient conversion of HA to 1,2-PDO by *E. coli* cells in a medium containing glycerol (Gonzalez et al., 2007 and provisional application 60/867,581). The amount of glycerol consumed is minimum and the stoichiometric conversion of HA to 1,2-PDO is achieved in a very short fermentation.

The results described above and shown in the FIGS. 4 and 5 clearly demonstrate the feasibility of developing a platform for the production of fuels and reduced chemicals from glycerol. Additional products whose production via glycerol fermentation would be advantageous include propanolamides, propionic acid, butanol, etc (Gonzalez et al., 2007). These processes would enable the implementation of true biorefineries and revolutionize the biofuel industry by greatly improving its economics.

REFERENCES

All references are listed herein for the convenience of the reader. Each is incorporated by reference in its entirety.

1. Bachler, C., et al., B. *Escherichia coli* dihydroxyacetone kinase controls gene expression by binding to transcription factor DhaR. EMBO J. 24:283-293 (2005).
2. Crabtree, S., et al., Optimize glycol production from biomass. Hydrocarbon Processing: 87-92 (2006).
3. Datsenko, K. A., Wanner. B. L. One-step inactivation of chromosomal genes in *Escherichia coli* K-12 using PCR products. Proc. Natl. Acad. Sci. U.S.A. 97:6640-5 (2000).
4. Dharmadi, Y., & R. Gonzalez. A better global resolution function and a novel iterative stochastic search method for optimization of HPLC separation. J. Chromatogr. A. 1070: 89-101 (2005).
5. Dharmadi, Y., et al., Anaerobic fermentation of glycerol by *Escherichia coli*: a new platform for metabolic engineering. Biotechnol. Bioeng. 94:821-829 (2006).
6. Gonzalez, R., et al., A New Paradigm for Glycerol Fermentation in *Escherichia coli* and other Enteric Bacteria and its Implications for the Biofuel Industry. Proc. Natl. Acad. Sci. USA. (In Press) (2007).
7. Jin, R. Z., et al., Experimental evolution of a novel pathway for glycerol dissimilation in *Escherichia coli*. J. Mol. Evol. 19:429-436 (1983).
8. Kang Y, et al., Systematic mutagenesis of the *Escherichia coli* genome. J Bacteriol 186:4921-4930 (2004).
9. Neidhardt, F. C., et al., Culture medium for enterobacteria. J. Bacteriol. 119:736-747 (1974).
10. Sambrook, J., et al., Molecular cloning: a laboratory manual, 2nd ed. (Cold Spring Harbor Laboratory Press, Cold Spring Harbor, N.Y., 1989).
11. Schomburg I., et al., BRENDA, the enzyme database: updates and major new developments. Nucleic Acids Res. D431-433 (2004).
12. Tang, J. C., et al., Immunochemical properties of NAD+-linked glycerol dehydrogenases from *Escherichia coli* and *Klebsiella pneumoniae*. J. Bacteriol. 152:1169-1174 (1982).
13. Tang, J. C., et al., Derepression of an NAD-linked dehydrogenase that serves an *Escherichia coli* mutant for growth on glycerol. J. Bacteriol. 152:1001-1007 (1982).
14. Tanaka, S., et al., Replacement of a phosphoenolpyruvate-dependent phosphotransferase by a nicotinamide adenine dinucleotide-linked dehydrogenase for the utilization of mannitol. J. Bacteriol. 93:642-648 (1967).
15. Tao, H., et al., Engineering a homo-ethanol pathway in *Escherichia coli*: increased glycolytic flux and expression levels of glycolytic genes during xylose fermentation. J. Bacteriol. 183:2979-2988 (2001).

What is claimed is:

1. A method to anaerobically ferment glycerol to produce a product, comprising: culturing a bacterial cell in a medium wherein said medium comprises at least 10 g/L glycerol as a carbon source, less than 10 mM potassium, less than 50 mM phosphate, CO2 greater than or equal to 10%, and a pH between 5.0 and 7.5, under anaerobic conditions such that glycerol is converted into a product, wherein said bacterial cell lacks a functional 1,3-propanediol pathway, but has a functional 1,2-propanediol (1,2-PDO) pathway, a functional type II glycerol dehydrogenase-dihydroxyacetone kinase pathway, and a functional $F_0F_1$-ATPase pathway to couple ATP synthesis with a proton pump, wherein said product is selected from the group consisting of ethanol, succinic acid, formic acid, hydrogen, 1,2-PDO, propanolamides, propionic acid, and butanol.

2. The method of claim 1, wherein the medium is supplemented with hydroxyacetone (HA), but not with tryptone.

3. The method of claim 1, wherein the medium is supplemented with 30 mM HA.

4. The method of claim 1, wherein the bacterial cell also has a functional formate-hydrogen lyase (FHL) pathway to disproportionate formate to $CO_2$ and hydrogen when the pH of the medium is less than or equal to 6.5.

5. The method of claim 1, wherein the $CO_2$ is at least 20% when the pH is about 7.5.

6. The method of claim 1, wherein the medium has less than or equal to 2 mM potassium and less than or equal to 10 mM phosphate.

7. The method of claim 1, wherein the medium has less than or equal to 1 mM potassium and less than or equal to 5 mM phosphate.

8. The method of claim 1, wherein the medium has less than or equal to 1 mM potassium and less than or equal to 2 mM phosphate.

9. The method of claim 8, wherein the pH is about 6.3 and the medium is sparged with an inert gas and said product is ethanol and hydrogen.

10. The method of claim 9, wherein a glycerol dehydrogenase and a dihydroxyacetone kinase are overexpressed, a phosphate acetyltransferase and a fumarate reductase are inactivated, the glycerol is crude glycerol and the medium further comprises corn steep liquor, but not tryptone.

11. The method of claim 8, wherein the bacterial cell lacks a functional FHL enzyme, the pH is about 7 and the medium is sparged with an inert gas, and said product is ethanol and formate.

12. The method of claim 11, wherein a glycerol dehydrogenase and a dihydroxyacetone kinase are overexpressed, a phosphate acetyltransferase and a fumarate reductase are inactivated, the glycerol is crude glycerol, and the medium further comprises corn steep liquor, but not tryptone.

13. The method of claim 8, wherein said bacterial cell lacks a native PEP dependent dihydroxyacetone kinase, and expresses an ATP dependent dihydroxyacetone kinase from *C. freundii*, and said product is succinate.

14. The method of claim 13, wherein the medium comprises 10-20% $CO_2$ and the pH is 6-7.5.

15. The method of claim 14, wherein a native glycerol dehydrogenase and a *C. freundii* dihydroxyacetone kinase are overexpressed, a native phosphoenolpyruvate carboxylase is inactivated, a phosphoenolpyruvate carboxykinase from *E. coli* or *A. succinogenes* is overexpressed, a phosphate acetyltransferase and alcohol dehydrogenase inactivated, the glycerol is crude glycerol and the medium further comprises corn steep liquor.

16. The method of claim 8, wherein a native glycerol dehydrogenase and a dihydroxyacetone kinase are overexpressed, and said product is 1,2-PDO.

17. The method of claim 16, wherein the native PEP dependent dihydroxyacetone kinase is replaced by *C. freundii* ATP dependent dihydroxyacetone kinase and enzymes methylglyoxal synthase, glycerol dehydrogenase, and methylglyoxal reductase are all overexpressed.

18. The method of claim 16, wherein an engineered or naturally occurring glycerol dehydratase capable of converting glycerol into hydroxyacetone is overexpressed.

19. A method of producing 1,2-PDO comprising: culturing a bacterial cell in a medium wherein said medium comprises at least 10 g/L glycerol as a carbon source, less than 10 mM potassium, less than 50 mM phosphate, CO2 greater than or equal to 10%, and a pH between 5.0 and 7.5, under anaerobic conditions such that glycerol is converted into 1,2-PDO, wherein said bacterial cell lacks a functional 1,3-propanediol pathway, but has a functional 1,2-propanediol pathway, a functional type II glycerol dehydrogenase-dihydroxyacetone kinase pathway, and a functional F0F1-ATPase pathway to couple ATP synthesis with a proton pump, and isolating 1,2-PDO from said cells or said medium.

20. The method of claim 19, wherein native PEP-dependent DHAK gene is inactivated and wherein ATP-dependent DHAK and glycerol dehydrogenase (gldA) genes are overexpressed.

21. The method of claim 20, wherein a gene encoding an enzyme selected from the group consisting of methylglyoxal synthase, glycerol dehydrogenase, and methylglyoxal reductase and combinations thereof is overexpressed.

22. The method of claim 19, wherein a gene encoding an enzyme selected from the group consisting of glycerol kinase, NAD+/NADP+-dependent glycerol dehydrogenase, NAD+/NADP+-dependent glycerol-3-P dehydrogenase, NAD+/NADP+-dependent glyceraldehyde dehydrogenase, NAD+/NADP+-dependent pyruvate dehydrogenase, NADH to NADPH transhydrogenase, propanediol oxidoreductase and combinations thereof is overexpressed.

23. The method of claim 19, wherein an engineered or native glycerol dehydratase (GD) gene for the conversion of glycerol into HA is expressed, individually or in combination with glycerol dehydrogenase gene overexpression.

24. The method of claim 19, wherein said medium comprises HA.

25. The method of claim 21, wherein a aldehyde/alcohol dehydrogenase (adhE) gene, a phosphoacetyltransferase (pta) gene, or a fumarate reductase (frd) gene and combinations thereof are knocked-out.

26. The method of claim 20, wherein engineered strains are subjected to a mutagenesis and selection in either continuous or sequential batch systems with selection of high-performing strains.

27. The method of claim 26, wherein said selection is conducted in the presence of decreasing amounts of oxygen and/or nitrate.

28. A method to anaerobically ferment glycerol to produce a product, comprising:
culturing a bacterial cell in a medium wherein said medium comprises at least 10 g/L glycerol as a carbon source, less than 10 mM potassium, less than 50 mM phosphate, CO2 greater than or equal to 10%, and a pH between 5.0 and 7.5, under anaerobic conditions such that glycerol is converted into a product,
wherein said bacterial cell:
i) lacks a glycerol dehydratase or a 1,3-PDO reductase or both and cannot make a 1,3-propanediol,
ii) has a methylglyoxal synthase, a aldo-keto reductase and a glycerol dehydrogenase and can make a 1,2 PDO,
iii) has a type II glycerol dehydrogenase and a dihydroxyacetone kinase and can make a dihydroxyacetone phosphate from said glycerol,
iv) has a formate dehydrogenase and a hydrogenase and can disproportionate formate to $CO_2$ and hydrogen, and
v) has a $F_0F_1$ ATP synthase and can couple ATP synthesis with a proton pump;
wherein said product is selected from the group consisting of ethanol, succinic acid, formic acid, hydrogen, 1,2-PDO, propanolamides, propionic acid, and butanol.

* * * * *